United States Patent [19]

Nicolau et al.

[11] Patent Number: 4,652,683

[45] Date of Patent: Mar. 24, 1987

[54] PROCESS FOR PRODUCING 2-HYDROXYPHENYL LOWER ALKYL KETONES

[75] Inventors: Ioan Nicolau; Adolfo Aguiló, both of Corpus Christi, Tex.

[73] Assignee: Celanese Corporation, New York, N.Y.

[21] Appl. No.: 803,195

[22] Filed: Dec. 2, 1985

[51] Int. Cl.$^4$ ............................................. C07C 45/46
[52] U.S. Cl. ..................................... 568/319; 560/129
[58] Field of Search ................. 568/319, DIG. 25 M; 560/129

[56] References Cited

U.S. PATENT DOCUMENTS

| 3,354,221 | 11/1967 | Landis et al. | 260/592 |
| 3,907,915 | 9/1975 | Chang et al. | 260/668 R |
| 4,283,573 | 8/1981 | Young | 568/794 |
| 4,291,185 | 9/1981 | Koeding | 585/467 |
| 4,371,714 | 2/1983 | Young | 568/628 |
| 4,448,983 | 5/1984 | Young | 560/241.1 |

*Primary Examiner*—James H. Reamer
*Attorney, Agent, or Firm*—M. Turken; D. R. Cassady

[57] ABSTRACT

A process is provided for the production of 2-hydroxyphenyl lower alkyl ketones, e.g. 2-hydroxyacetophenone, by reacting phenol and a lower alkanoic acid, e.g. acetic acid or an ester of phenol and a lower alkanoic acid, e.g. phenyl acetate, in the presence of a silicalite catalyst containing about 700 to 14000 ppm of alumina, which has been calcined at least once from the as synthesized form. The reaction is preferably conducted in the vapor phase in the presence of an inert gas such as nitrogen.

11 Claims, No Drawings

PROCESS FOR PRODUCING 2-HYDROXYPHENYL LOWER ALKYL KETONES

This invention relates to a process for producing 2-hydroxyphenyl lower alkyl ketones such as 2-hydroxyacetophenone.

BACKGROUND OF THE INVENTION

Compounds such as 2-hydroxyphenyl lower alkyl ketones, e.g. 2-hydroxyacetophenone (2-HAP) are possible intermediates for a variety of products having different end uses. Thus 2-HAP may be converted into catechol (1,2-dihydroxybenzene) by first reacting the 2-HAP to form the monoacetate ester of catechol using a "Baeyer-Villiger" oxidation as disclosed, for example in application Ser. No. 661,552, filed Oct. 17, 1984 and the references cited therein, and then converting the monoacetate ester to catechol by hydrolysis, e.g. as disclosed in the previously cited application Ser. No. 661,552, or by transesterification as disclosed in Ser. No. 689,533, filed Jan. 7, 1985 and the references cited therein. Alternatively, the 2-HAP can be converted into guaiacol by first methylating it to form 2-methoxyacetophenone, and then obtaining the acetate ester of the monomethyl ether of catechol by a Baeyer-Villiger oxidation and the guaiacol by hydrolysis or transesterification as previously described for catechol. Aspirin may be made from 2-HAP by first acetylating it with acetic anhydride to yield 2-acetoxyacetophenone and oxidizing the latter compound with a transition metal catalyst to form aspirin; these reactions are disclosed in application Ser. No. 633,832 filed July 24, 1984 and the references cited therein.

The reaction of phenol and acetic acid under certain specifically defined conditions to obtain hydroxyacetophenones is disclosed in application Ser. No. 06/716,016 filed Mar. 26, 1985. Cited in this application are the following published references with teachings of the reaction of phenol and acetic acid to form 4-hydroxyacetophenone (4-HAP), as described:

Dann and Mylius in a dissertation included as part of a series of Reports from the Institute for Applied Chemistry of the University of Erlangen, received for publication on Jan. 7, 1954 and published in Annalen der Chemie 587 Band, pages 1 to 15, disclose the reaction of phenol and glacial acetic acid in the presence of hydrogen fluoride to produce 4-hydroxyacetophenone (4-HAP) in a yield of 61.6%. This reaction may be conventionally characterized as a Friedel-Crafts acetylation of phenol with acetic acid as the acetylating agent.

Simons et al, Journal of the American Chemical Society, 61, 1795 and 1796 (1939) teach the acylation of aromatic compounds using hydrogen fluoride as a condensing agent and in Table 1 on page 1796 show the acetylation of phenol with acetic acid to produce p-hydroxyacetophenone (4-HAP) in 40% yield.

None of the foregoing disclosures, however, teach any method of reacting phenol with acetic acid in the presence of a silicalite catalyst to obtain a product comprising of 2-HAP.

The prior art also discloses the Fries rearrangement of phenyl acetate to form hydroxyacetophenones. For example, the previous cited Dann and Mylius article shows the rearrangement of phenyl acetate in hydrogen fluoride to 4-hydroxyacetophenone, with a maximum yield of 81% after 24 hours of reaction time, and report a yield of 92% stated to be obtained by K. Weichert as reported in Angewandte Chemie 56, 338 (1943). Although Dann and Mylius suggest that the difference in yields may be at least partly due to the previous ignoring by Weichert of the accompanying 2-hydroxyacetophenone, the latter is nevertheless produced in only minor amounts as compared with the 4-hydroxyacetophenone.

Davenport et al, U.S. Pat. No. 4,524,217, disclose a process for the production of N-acetyl-para-aminophenol (acetaminophen) including the Fries rearrangement of phenyl acetate with a hydrogen fluoride catalyst to produce a preponderance of 4-hydroxyacetophenone.

Thus, none of these references discloses a method for carrying out a Fries rearrangement of phenylacetate in the presence of a silicalite catalyst to produce 2-hydroxyacetophenone.

SUMMARY OF THE INVENTION

In accordance with this invention, phenol is reacted with a lower alkanoic acid, e.g. acetic acid, or an ester of phenol and a lower alkanoic acid, e.g. phenyl acetate, is reacted in contact with a silicalite catalyst containing alumina ($Al_2O_3$) within a defined range as hereinafter defined, said catalyst having been calcined from the as synthesized form at least once, to produce a product comprising a 2-hydroxyphenyl lower alkyl ketone, e.g. 2-hydroxyacetophenone (2-HAP). The exact amount of the 2-hydroxyphenyl ketone in the product may vary depending on conditions with most of the remainder being the corresponding 4-hydroxyphenyl ketone, e.g. 4-hydroxyacetophenone (4-HAP).

The reaction between phenol and lower alkanoic acid to produce hydroxyphenyl lower alkyl ketones proceeds in accordance with the following equation:

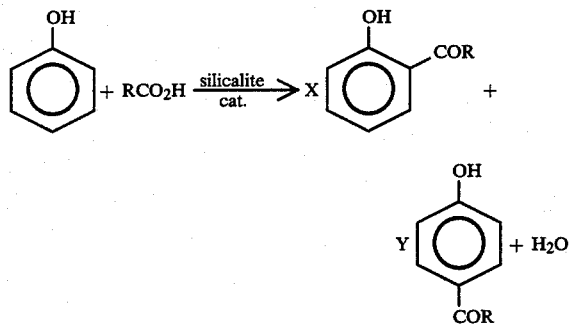

where R is lower alkyl, and X and Y add up to 1 and are the mole fractions of the 2-hydroxyphenyl and 4-hydroxyphenyl ketones respectively based on the total amount of hydroxyphenyl ketones produced in the reaction.

If the lower alkanoic acid is acetic acid, i.e., R is methyl, the reaction proceeds as in the following equation:

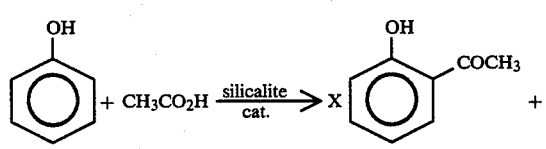

-continued

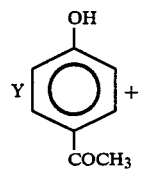

The reaction of an ester of phenol with a lower alkanoic acid in the presence or absence of a free lower alkanoic acid may be assumed to be Fries rearrangement which proceeds in accordance with the following equation:

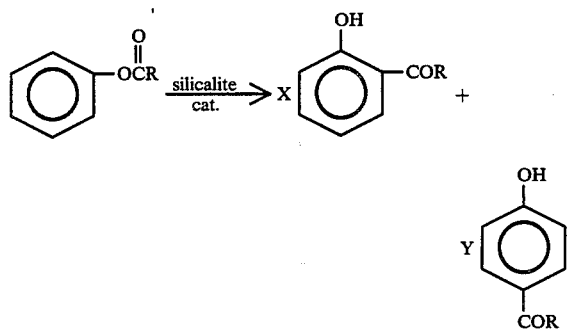

where R, X and Y have the definitions given previously.

If the ester reacted is phenyl acetate, the reaction proceeds as follows:

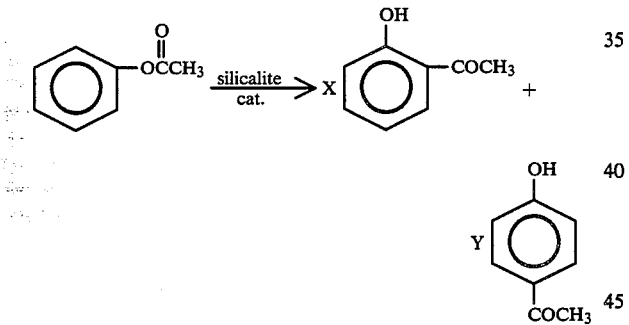

Preferably, R in the foregoing equations contains 1 to 3 carbon atoms so that the lower alkanoic acid in free form or as the acid forming the ester with phenol is acetic, propionic, n-butyric or isobutyric acid. The preferred acid is acetic acid which yields 2-HAP as the preferred product.

If an ester of phenol and a lower alkanoic acid is used as the starting material, the reaction may be carried out in the presence of a free lower alkanoic acid, e.g. acetic acid as an additive for the reaction. The acid may be the same as or different from the acid used to prepare the phenolic ester starting material.

The silicalites utilized as catalysts in the process of this invention are crystalline silica polymorphs, many of which are similar to those described, for example, in U.S. Pat. No. 4,061,724, issued to Grose et al on Dec. 7, 1977, the entire disclosure of which is incorporated by reference.

The X-ray powder diffraction pattern of many of the silicalites utilized in the present invention (600° C. calcination in air for one hour) has as its six strongest lines (i.e. interplanar spacings) those set forth in Table A below, wherein "S"=strong and "VS"=very strong.

TABLE A

| d-A | Relative Intensity |
|---|---|
| 11.1 ± 0.2 | VS |
| 10.0 ± 0.2 | VS |
| 3.85 ± 0.07 | VS |
| 3.82 ± 0.07 | S |
| 3.76 ± 0.05 | S |
| 3.72 ± 0.05 | S |

The silicalites utilized as catalysts in the present invention have in the as-synthesized form a specific gravity at 25° C. of 1.99±0.08 cc as measured by water displacement. In the calcined (600° C. in air for 1 hour) form silicalite has a specific gravity of 1.70 g±0.08 g cc. With respect to the mean refractive index of silicalite crystals, values obtained by measurement of the as-synthesized form and the calcined form (600° C. in air for 1 hour) are, respectively, 1.48±0.01 and 1.39±0.01.

Crystals of silicalite in both the as-synthesized and calcined form are orthorhombic and have the following unit cell parameters: a=20.05 A, b=20.0 A, c=13.4 A, with an accuracy of ±0.1 A on each of the above values. The pore diameter of silicalite is about 5 to 6 Angstrom units and its pore volume is 0.18±0.02 cc./gram as determined by adsorption.

The pores of the silicalite particles have a pattern providing for easy access to vapors and liquids intended to be treated. For example the pores may be in the form of zig-zag channels cross-linked by straight channels.

The preparation of silicalite may be accomplished, for example by the hydrothermal crystallization of a reaction mixture comprising water, a source of silica and an alkylonium compound at a pH of 10 to 14 to form a hydrous crystalline precursor, and subsequently calcining that precursor to decompose alkylonium moieties present therein.

The alkylonium cation is suitably supplied to the reaction system by a compound preferably soluble in the reaction mixture and which contains a quaternary cation generally expressed by the formula

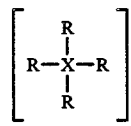

wherein R is an alkyl radical containing from 2 to 6 carbon atoms and X represents either phosphorus or nitrogen. Preferably R is ethyl, propyl or n-butyl, especially propyl, and X is nitrogen. Illustrative compounds include tetraethylammonium hydroxide, tetrapropylammonium hydroxide, tetrabutylammonium hydroxide, tetrabutylphosphonium hydroxide and the salts corresponding to the aforesaid hydroxides, particularly the chloride, iodide and bromide salts, for example, tetrapropylammonium bromide. The quaternary compounds can be supplied to the reaction mixture per se or can be generated in situ, such as by the reaction of tertiary amines with alkyl halides or sulfates.

When the quaternary cation is provided to the system in the form of the hydroxide in sufficient quantity to establish a basicity equivalent to the pH of 10 to 14, the reaction mixture need contain only water and a reactive form of silica as additional ingredients. In those cases in which the pH is required to be increased to above 10, ammonium hydroxide or alkali metal hydroxides can be suitably employed for that purpose, particularly the hydroxides of lithium, sodium or potassium. It has been found that not more than 6.5 moles of alkali metal oxide per mole-ion of quaternary cation is required for this purpose even if none of the quaternary cation is provided in the form of its hydroxide.

The source of silica in the reaction mixture can be wholly or in part alkali metal silicate out should not be employed in amounts greater than that which would change the molar ratio of alkali metal to quaternary cations set forth above. Other silica sources include solid reactive amorphous silica such as fumed silica, silica sols and silica gel.

The silicalites contemplated for use in this invention generally contain about 700 to 14,000 ppm of alumina corresponding to a $SiO_2$ to $Al_2O_3$ ratio of about 120 to 1450, preferably about 5000 to 7000 ppm of alumina corresponding to a $SiO_2$ to $Al_2O_3$ ratio of about 240 to 340. The amount of alumina in the silicalite will generally depend to a large extent of the source of silica. For example, commercially available silica sols can typically contain from 500 to 700 ppm $Al_2O_3$, whereas fumed silicas can contain from 80 to 2000 ppm of $Al_2O_3$. Silicalites containing still larger amounts of alumina may be obtained by using other sources of silica with higher contents of alumina as is well-known in the art.

The quantity of silica in the reaction system should be from about 13 to 50 moles $SiO_2$ per mole-ion of the quaternary cation. Water should be present in an amount of from 150 to 700 moles per mole-ion of the quaternary cation.

Accordingly, in preparing the crystalline silicalite precursor, there is formed a reaction mixture having a pH of at least 10 which in terms of moles of oxides contains from 150 to 700 moles $H_2O$, from 13 to 50 moles non-crystalline $SiO_2$ and from 0 to 6.5 moles $M_2O$, wherein M is an alkali metal, for each mole of $Q_2O$ present, wherein Q is a quaternary cation having the formula $R_4X+$ in which each R represents hydrogen or an alkyl group containing from 2 to 6 carbon atoms and X is phosphorus or nitrogen.

The order in which the reagents are admixed is not a critical factor. The reaction mixture is maintained at a temperature of from about 100° to 250° C. under autogeneous pressure until crystals of the silicalite precursor are formed, ordinarily from about 50 to 150 hours. The crystalline product is recovered by any convenient means such as filtration. Advantageously the product is washed with water and can be dried in air at about 100° C.

When alkali metal hydroxide has been employed in the reaction mixture, alkali metal moieties appear as impurities in the crystalline product. Although the form in which these impurities exist in the crystalline mass has not yet been determined, they are not present as cations which undergo reversible exchange. The quaternary cation moiety is quite readily thermally decomposed and removed by calcination in an oxidizing atmosphere (air) or inert atmosphere at temperatures of from about 480° C. to 1000° C. for a period sufficient to obtain the desired silicalite, usually about 1 to 6 hrs. The residual alkali metal in the product can be removed or reduced by washing with alkali metal halide solution or an aqueous acid solution of sufficient strength such as hydrochloric acid. The crystal structure is not otherwise affected by contact with strong mineral acids even at elevated temperatures due to the lack of acid-soluble constituents in its crystal structure.

The reaction may be carried out in the vapor or liquid phase under a wide variety of conditions. Reaction temperatures may be employed, for example in the range of about 200° to 350° C., preferably about 250° to 320° C. The pressure is generally uncritical to the reaction and subatmospheric, atmospheric or superatmospheric pressures maybe employed. In most cases, however, the pressure of the reaction will be in the range of about 1 to 25 atmospheres absolute. Generally, it is most advantageous to carry out the reaction in the vapor phase, in which case the tempature may be, for example, in the range of about 250° to 320° C., preferably about 280° to 300° C. at a pressure, for example of about 1 to 3 atmospheres, more preferably about 1 to 2 atmospheres, and most preferably about 1.5 to 1.7 atmospheres and an actual catalyst contact time of about 3 to 25 preferably about 5 to 15 seconds.

Although the reaction between phenol and lower alkanoic acid consumes one mole of phenol per mole of acid to produce a mole of hydroxyphenyl lower alkyl ketones, the actual molar ratio of phenol to alkanoic acid in the feed stream may be varied between wide limits, e.g. from about 100:1 to 1:100. It is preferred however that such ratio be in the range of about 1:20 to 1:1.

A lower alkanoic acid when employed as an additive or solvent for the reaction may be added, for example, in an amount of about 1 to 5 moles, preferably about 1 to 2 moles per mole of phenol or phenol ester in the feed.

If the feed compounds are in the vapor state at the reaction temperature, then they can be fed in undiluted state or diluted with a relatively inert carrier gas, such as nitrogen, argon, helium, and the like. The inert gas may be used, for example, in an amount of about 5 to 95 mol %, preferably about 25 to 35 mol % based on the total feed. Likewise, if the reactants are liquid at the reaction temperature, then they also can be used either alone or with a suitable diluent, e.g. sulfolane or a paraffinic hydrocarbon containing, for example, about 12 to 18 carbon atoms.

Typically, the catalyst is employed in a fixed bed reactor e.g. in the shape of an elongated pipe or tube where the reactants, typically in the vapor form, are passed over or through the catalyst. Other reactors, such as fluid or ebullient bed reactors, can be employed, if desired.

The following examples further illustrate the invention:

EXAMPLES 1 to 6

These examples illustrate the production of 2-hydroxyacetophenone (2-HAP) from phenol (PhOH) and acetic acid (HOAc).

The catalyst used was a silicalite sold by Union Carbide Corporatron under the designation "S-115". It was prepared as described in U.S. Pat. No. 4,061,724 and was composed of more than 99 wt.% of silica containing about 6500 to 7000 ppm of alumina such that the $SiO_2$ to $Al_2O_3$ ratio was about 241 and the catalyst contained about 0.03 wt.% of the total or sodium and potassium.

The crystal structure of the silicalite was made up ot a tetrahedral framework, which contained a large fraction of five-membered rings of silicon-oxygen tetrahedra. Its channel system was composed of near-circular zig-zag channels (free cross-section 5.4±0.2A) crosslinked by elliptical straight channels witn a free cross-section of 5.75×5.15 A. Both channels were defined by 10 rings. The X-ray powder diffraction pattern was as defined in Table A of U.S. Pat. No. 4,061,724.

Other properties of the silicalite were a pore volume of about 0.19 cc/gm and a crystal density of about 1.76 cc/gm.

The 2-HAP product was produced by the acetylation of phenol with acetic acid in vapor phase over the silicalite catalyst at 300° C. and 7 psig total pressure. The reaction mixture (phenol and acetic acid) was fed by means of a Milton Roy liquid delivery pump at about 0.26 ml/min into a flasher where the mixture was vaporized at 180° C. into a stream of nitrogen (50 cc/min). The vapor mixture was carried through stainless steel electrically heated lines to the 0.364 inch i.d. U-tube stainless steel reactor immersed in a sandbath. The reactor pressure was maintained constant by means of a back pressure regulator. The catalyst volume was varied from 14 to 56 cc as −20+30 mesh particles. The reactor effluent was condensed in a chilled water condenser followed by two dry ice-isopropanol traps, weighted and analyzed by a flame ionization GC using a Carbowax 20M capillary column. Water in the liquid product was determined by the Karl Fisher method. The permanent gases were collected in plastic bags and analyzed by mass spectroscopy. The total dry vent was estimated by measuring periodically the flow rate with a soap flowmeter. The duration of a run was in general about 120 minutes. Before every run the microunit was purged with nitrogen to remove any traces of air.

The process conditions varied in the examples were catalyst volume and age, total vapor feed flow rate, catalyst contact time under the conditions of reaction (CT. TIME) and ratio of phenol to acetic acid in the reaction mixture. Table I shows the specific conditions of the examples as well as the results obtained including phenol conversion, selectivities of the various product components based on phenol conversion, the space time yield (STY) of 2-HAP and the mass and carbon accountabilities.

Percent conversion is calculated by dividing the moles of phenol reacted times 100 by the moles of phenol fed. The percent selectivity is calculated by dividing the moles of the specific product formed times 100 by by the moles of phenol converted. The percent mass accountability (ACCT.% MASS) is the weight of liquid and gas product divided by the weight of liquid fed times 100. The reacted carbon accountability (ACCT.% CARBON) is the total moles of carbon containing products formed divided by the total moles of reactants converted times 100. In addition to 2-HAP and 4-HAP, Table I shows the selectivities to phenyl acetate (PhOAc), 4-acetoxyacetophenone (4-AAP), 2-methylchromone (2-MCH) and 4-methylcoumarin (4-MC). Finally small amounts of byproducts (in addition to those mentioned in the tables) such as acetone, carbon dioxide, carbon monoxide and water were also formed.

TABLE I

| EXAMPLE | CATALYST VOL. CC | AGE HRS | FLOW RATE (TOTAL) CC/MIN | CT. TIME, SEC | FEED, MOLE % PHOH | HOAC | N2 | PHOH CONV. |
|---|---|---|---|---|---|---|---|---|
| 1 | 56 | 9.7 | 137.9 | 18.7 | 31.1 | 31.2 | 37.0 | 31.1 |
| 2 | 14 | 1.3 | 136.7 | 4.7 | 31.5 | 31.6 | 36.3 | 28.1 |
| 3 | 28 | 4.3 | 145.8 | 8.8 | 32.4 | 32.4 | 34.6 | 29.6 |
| 4 | 28 | 3.0 | 153.9 | 8.4 | 5.9 | 61.0 | 32.0 | 66.6 |
| 5 | 28 | 3.8 | 150.4 | 8.6 | 11.1 | 55.3 | 33.0 | 54.1 |
| 6 | 28 | 1.1 | 145.3 | 8.9 | 21.4 | 42.9 | 34.6 | 40.0 |

| EXAMPLE | SELECTIVITY % | | | | | | 2-HAP STY G/L/HR | ACCT. % | |
|---|---|---|---|---|---|---|---|---|---|
| | 2-HAP | 4-HAP | PHOAC | 4-AAP | 2-MCH | 4-MC | | MASS | CARBON |
| 1 | 59.2 | 3.5 | 38.3 | 0.3 | 0.1 | 0.1 | 47.0 | 100.7 | 100.5 |
| 2 | 45.2 | 3.5 | 37.0 | 0.4 | 0.1 | 0.1 | 130.4 | 99.4 | 90.8 |
| 3 | 48.9 | 2.8 | 35.0 | 0.4 | 0.1 | 0.1 | 81.4 | 90.9 | 93.8 |
| 4 | 47.4 | 2.9 | 32.3 | 1.0 | 0.4 | 0.1 | 34.1 | 99.9 | 93.2 |
| 5 | 45.7 | 2.9 | 33.7 | 0.8 | 0.2 | 0.1 | 50.2 | 97.2 | 81.6 |
| 6 | 45.1 | 2.4 | 29.0 | 0.3 | 0.1 | 0.1 | 66.5 | 94.5 | 86.4 |

EXAMPLES 7 to 13

The procedure of Examples 1 to 6 was followed except that the feed reactant was phenyl acetate either in the presence of acetic acid additive or solvent (Examples 7 to 11) or without any acetic acid (Examples 12 and 13), and the catalyst volume was 28 cc. The process conditions and results of these examples are shown in Table II, wherein the percent conversions and selectivities are based on phenyl acetate.

TABLE II

| EXAMPLE | CATALYST AGE/HRS | FEED, MOLE % HOAC | PHOAC | H2O | N2 | CT. TIME SEC | CONV. % | SELECTIVITY % 2-HAP | 4-HAP | 4-AAP | 2-MCh | PHOH | 2-HAP STY G/L/HR | ACC % MASS | C |
|---|---|---|---|---|---|---|---|---|---|---|---|---|---|---|---|
| 7 | 1.3 | 56.8 | 5.5 | 0.5 | 37.2 | 8.2 | 67.8 | 43.6 | 3.9 | 3.1 | 0.4 | 37.0 | 30.5 | 93.5 | 99.2 |
| 8 | 4.2 | 59.0 | 5.7 | 0.5 | 34.7 | 8.5 | 54.7 | 30.6 | 6.6 | 10.4 | 2.1 | 29.8 | 17.8 | 96.7 | 77.7 |
| 9 | 6.2 | 28.0 | 27.8 | 0.3 | 44.0 | 10.5 | 20.7 | 12.4 | 6.1 | 27.9 | 0.3 | 9.8 | 10.4 | 96.8 | 64.0 |
| 10 | 1.1 | 27.8 | 27.6 | 0.3 | 44.3 | 10.5 | 44.1 | 25.5 | 9.9 | 17.6 | 0.3 | 35.4 | 45.3 | 94.2 | 85.8 |
| 11 | 3.1 | 27.9 | 27.7 | 0.3 | 44.0 | 10.4 | 31.3 | 17.8 | 9.4 | 21.4 | 0.2 | 40.5 | 22.8 | 101.7 | 88.2 |
| 12 | 1.4 | 0 | 49.6 | 0.4 | 50.0 | 12.9 | 22.9 | 14.4 | 11.1 | 24.1 | 0.2 | 24.0 | 19.4 | 101.3 | 76.5 |

TABLE II-continued

| EXAMPLE | CATALYST AGE/ HRS | FEED, MOLE % | | | | CT. TIME SEC | CONV. % | SELECTIVITY % | | | | | 2-HAP STY G/L/HR | ACC % | |
|---|---|---|---|---|---|---|---|---|---|---|---|---|---|---|---|
| | | HOAC | PHOAC | H20 | N2 | | | 2-HAP | 4-HAP | 4-AAP | 2-MCh | PHOH | | MASS | C |
| 13 | 3.8 | 0 | 49.8 | 0.4 | 49.8 | 12.9 | 9.1 | 9.1 | 5.7 | 26.5 | 0.4 | 17.8 | 4.9 | 99.3 | 64.3 |

Examples 14 and 15 illustrate the effect of a silica binder on the catalytic activity of a S-115 catalyst in the form of 1/8 inch extrudates containing such a binder.

EXAMPLE 14

The procedure of Examples 7 to 13 was followed except that the catalyst was the S-115 used in those examples blended with 20 wt. % conventional silica (as binder) and containing 0.2 wt. % of the total of sodium and potassium, said weight percents being based on the total catalyst weight. The catalyst volume was 28 cc and its age was 1.1 hours. The feed flowed at a rate of 118.9 cc/min and was composed of 28.9 mol % of phenyl acetate, 29.1 mol % of acetic acid and 42.0 mol % nitrogen and the catalyst contact time was 10.8 sec. The reaction resulted in a percent conversion or phenyl acetate of 17.8% at the following selectivities: 2-HAP 2.3%; 4-HAP 9.0%; 4-AAP 16.0%; and PhOH 78.7%; an STY to 2-HAP of 1.7 g/liter/hr, a mass accountability of 99.6%; and a reacted carbon accountability of 91.9%.

EXAMPLE 15

The procedure of Examples 1 to 6 and 14 was followed except that the catalyst was treated with HCl such that the total of the sodium and potassium content was 0.1 wt. %, the alumina was 5500 ppm and the $SiO_2$ to $Al_2O_3$ ratio was about 307. The catalyst age at the beginning of the reaction was 1.0 hours, the feed flowed at a rate of 137.4 cc/min and was composed of 31.4 mol % of phenol, 32.1 mol % of acetic acid and 36.5 mol % of nitrogen, and the catalyst contact time was 9.4 sec. The reaction resulted in a percent conversion of phenol of 27.5% at the following percent selectivities: 2-HAP 3.4%; 4-HAP 5.2%; 4-AAP 1.4%; 2-MCH 0.1%; and PhOAc 75.8%; an STY to 2-HAP of 4.8 g/liter/hr, a mass accountability of 100.3% and a reacted carbon accountability of 93.8%.

We claim:

1. A process comprising reacting phenol and a lower alkanoic acid or an ester of phenol and a lower alkanoic acid in contact with a silicalite catalyst containing about 700 to 14000 ppm of alumina, said catalyst having been calcined from the as synthesized form at least once, to produce a product comprising a 2-hydroxyphenyl lower alkyl ketone.

2. The process of claim 1 wherein said lower alkanoic acid in both occurrences is acetic acid, said 2-hydroxyphenyl lower alkyl ketone is 2-hydroxyacetophenone and the reaction occurs in the vapor phase.

3. The process of claim 2 wherein phenol and acetic acid are reacted.

4. The process of claim 2 wherein phenyl acetate is reacted in the presence of free acetic acid.

5. The process of claim 2 wherein the reaction occurs in the presence of an inert gas.

6. The process of claim 5 wherein said inert gas is nitrogen.

7. The process of claim 1 wherein said calcined srlicalite contains about 5000 to 7000 ppm of alumina.

8. The process of claim 1 wherein said calcined silicalite has a mean refractive index of 1.39±0.01 and a specific gravity at 25° C. of 1.70±0.08.

9. The process of claim 1 wherein the six strongest d-values of the X-ray powder diffraction pattern of said calcined silicalite are as set forth in the following table wnerein "S"=strong and "VS"=very strong

| d-A | Relative Intensity |
|---|---|
| 11.1 ± 0.2 | VS |
| 10.0 ± 0.2 | VS |
| 3.85 ± 0.07 | VS |
| 3.82 ± 0.07 | S |
| 3.76 ± 0.05 | S |
| 3.72 ± 0.05 | S |

10. The process of claim 1 wherein the material reacting consists of said phenol and alkanoic acid with a molar ratio of phenol to alkanoic acid in the range of about 100:1 to 1:100, or said ester of phenol and lower alkanoic acid in the presence or absence of a free alkanoic acid as additive, the temperature of reaction is in the range of about 200° to 350° C., the pressure of reaction is in the range of about 1 to 25 atmospheres absolute, and the contact time of reactants and catalyst is in the range of about 3 to 25 seconds.

11. The process of claim 8 wherein the material reacting consists of said phenol and acetic with a mole ratio of phenol to acetic acid in the range of about 1:20 to 1:1, or phenyl acetate in the presence of absence of free acetic acid as additive, the temperature of reaction is in the range of about 250° to 320° C., the pressure of reaction is in the range of about 1 to 25 atmospheres absolute, and the contact time of reactants and catalyst is in the range of about 3 to 25 seconds.

* * * * *